United States Patent [19]

Lieberman

[11] Patent Number: 5,312,428
[45] Date of Patent: May 17, 1994

[54] CORNEAL PUNCH AND METHOD OF USE

[76] Inventor: David M. Lieberman, 300 E. 51st St., Apt. 18B, New York, N.Y. 10022

[21] Appl. No.: 774,413

[22] Filed: Oct. 10, 1991

[51] Int. Cl.⁵ .......................................... A61B 17/16
[52] U.S. Cl. ..................................... 606/166; 128/898
[58] Field of Search ....................... 606/166, 4, 5, 6; 128/898

[56] References Cited

U.S. PATENT DOCUMENTS

| | | | |
|---|---|---|---|
| 4,018,228 | 4/1977 | Goosen | 128/305 |
| 4,205,682 | 6/1980 | Crock et al. | 128/305 |
| 4,236,519 | 12/1980 | LaRussa et al. | 128/305 |
| 4,336,805 | 6/1982 | Smirmaul | 128/310 |
| 4,423,728 | 1/1984 | Lieberman | 128/310 |
| 4,429,696 | 2/1984 | Hanna | 128/310 |
| 4,619,257 | 10/1986 | Linner et al. | 128/303 |
| 4,660,556 | 4/1987 | Swinger et al. | 606/166 |
| 4,718,420 | 1/1988 | Lemp | 606/166 |
| 4,739,761 | 4/1988 | Grandon | 128/305 |
| 4,865,033 | 9/1989 | Krumeich | 128/346 |
| 4,880,017 | 11/1989 | Soll | 128/898 |
| 4,884,570 | 12/1989 | Krumeich et al. | 606/166 |
| 5,006,123 | 4/1991 | Soll | 606/166 |
| 5,011,498 | 4/1991 | Krumeich | 606/166 |
| 5,092,874 | 3/1992 | Rogers | 606/666 |
| 5,152,759 | 10/1992 | Parel et al. | 128/395 |

Primary Examiner—Edgar S. Burr
Assistant Examiner—John S. Hilten
Attorney, Agent, or Firm—Anthony J. Casella; Gerald E. Hespos

[57] ABSTRACT

A corneal punch for cutting a portion of corneal tissue. The corneal punch includes a support stand including a base portion having a recess formed therein. First and second pins extend upwardly from the base portion and are constructed to receive a cutting block in a single rotational orientation relative to the support stand. A piston assembly having a cutting blade mounted thereon is movably mounted on the support stand. The piston assembly is rotationally locked relative to the support stand in order to prevent rotation of the piston assembly relative to the support stand during the cutting of corneal tissue. The cutting block has at least one mark placed thereon such that the orientation of the corneal tissue relative to the corneal punch can be controlled. A method for transplanting corneal tissue is also provided. The method includes the step of marking the corneal tissue to indicate the original rotational orientation of the corneal tissue and to indicate the eye from which the corneal tissue was taken. A corneal button is cut from the marked corneal tissue and then implanted in a recipient's left or right eye in a rotational orientation substantially the same as the original rotational orientation of the corneal tissue.

5 Claims, 6 Drawing Sheets

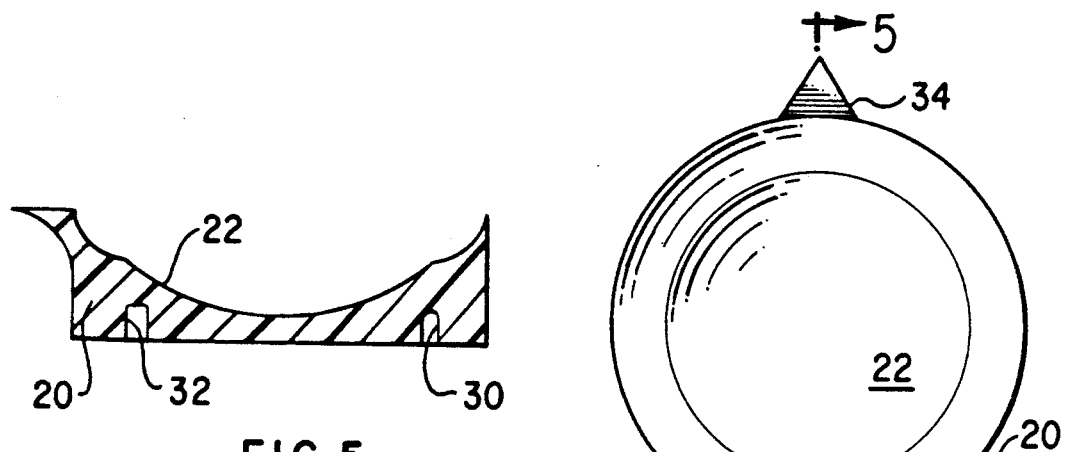
FIG. 5
FIG. 4
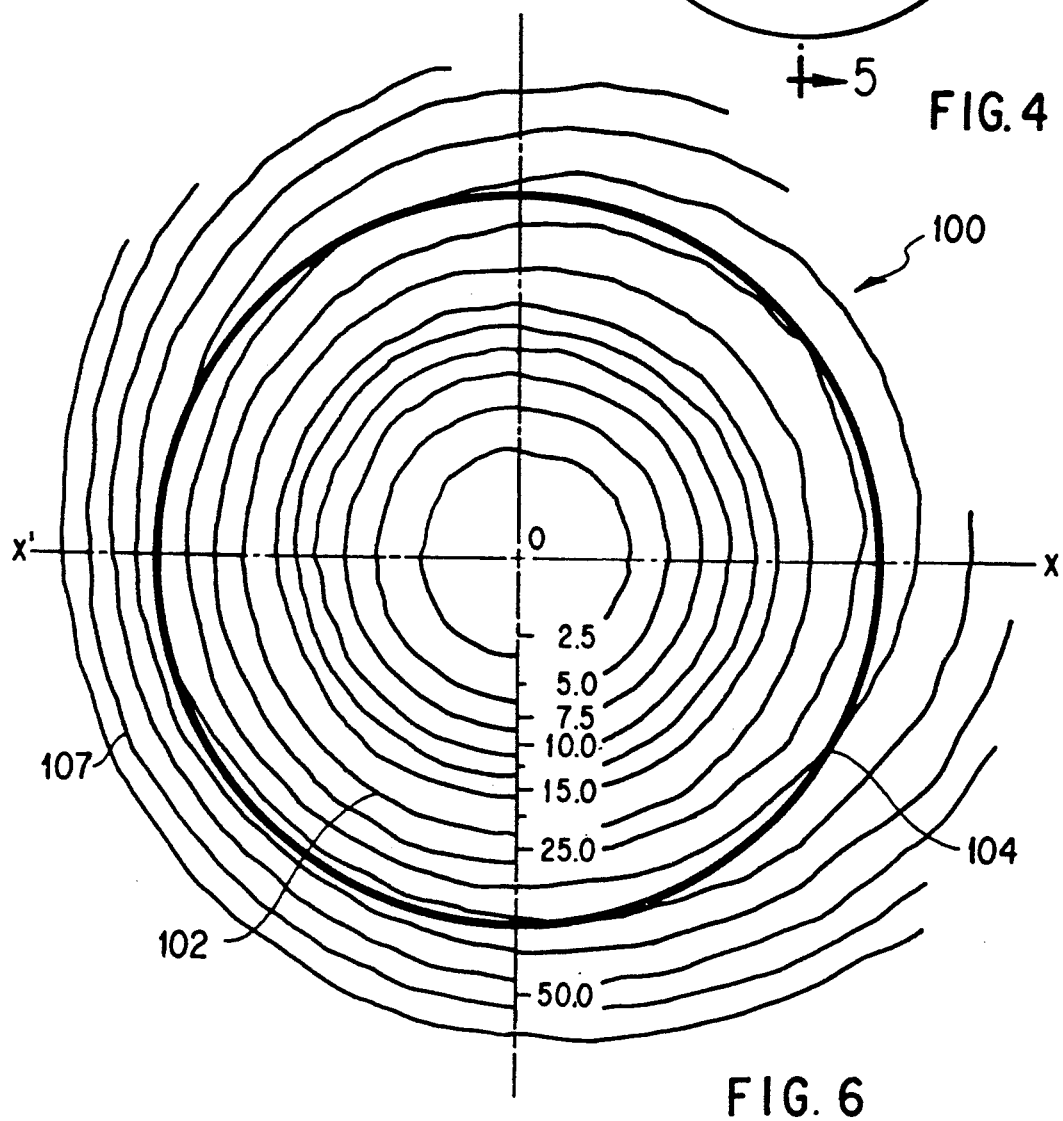
FIG. 6

CORNEAL PUNCH AND METHOD OF USE

FIELD OF THE INVENTION

The present invention relates to ophthalmic surgery and more particularly to a corneal punch and method of cutting the cornea of the eye for performing a corneal transplant.

BACKGROUND OF THE INVENTION

The cornea, the outer tissue of the eye, is frequently the subject matter of ophthalmic surgery. In a corneal transplant, for example, a central portion of the cornea of a patient's eye is surgically removed. Preferably, the surgical removal is by a cut that is parallel to the axis of the patient's eye. Typically, in the prior art, the surgical removal leaves a hole in the patient's eye that is circularly symmetric about the axis thereof.

The hole is filled by a central portion of a cornea of an eye of a donor. Analogous to the hole, the central portion of the donor's cornea is circularly symmetric about the axis of the donor's cornea. Moreover, when a cut of the donor's cornea is made to provide the control portion thereof, the cut is preferably parallel to the axis of the donor's cornea.

Usually, the cut of the donor's cornea is made by a hollow cylindrical blade that has a cutting edge at one end. The donor's cornea is placed upon a work surface of the fixture and the blade is advanced along its axis towards the donor's cornea.

The desired diameter of the cut of the donor's cornea is usually in the range of six and one-half millimeters to eleven millimeters. And, typically, the desired diameter of the cut of the donor's cornea is in the range of seven to nine millimeters.

The prior art has shown in U.S. Pat. No. 4,236,579, a corneal punch device having a corneal punch and fixture wherein the punch is suitable for use with round blades of various diameters so as to allow for the cutting of various sized donor's cornea.

However, such a corneal punch is not suitable for use wherein it is desirable to maintain the correct rotational orientation of the donor's cornea for transplantation onto a patient's cornea. Further, such a corneal punch is unsuitable for use with blades for cutting non-round or other than round holes in the donor's cornea while maintaining the correct rotational orientation of the donor's cut cornea to the opening or hole cut in the patient's cornea.

SUMMARY OF THE INVENTION

It is therefore an object of the invention to provide a corneal punch device which overcomes the disadvantages of the prior art corneal punch devices.

It is a further object of the invention to provide a corneal punch device wherein the punch, blade and cutting block are maintained or keyed in a fixed rotational orientation so that the rotational orientation of the cut corneal tissue can be determined and maintained, so that cut corneal tissue or button can be transplanted onto the patient's eye in the same rotational orientation as it existed in the donor's eye.

It is a further object of the invention to provide a corneal punch device which utilizes blades of either round or other than round configurations having various diameters and/or dimensions while maintaining the correct rotational orientation of the cut corneal tissue before, during and after the corneal punching operation.

It is a further object of the invention to provide a corneal punch device which utilizes separate left and right corneal blocks for the left or right donor's corneal tissue.

And, it is a further object of the invention to provide a method of performing corneal transplants wherein a donor's corneal tissue is marked with respect to the donor's left or right eyes and the rotational orientation so that the donor's corneal tissue can be reattached to the patient's correct left or right eye and maintain the same rotational orientation as it existed in the original donor's eye to limit the degree of surgically induced astigmatism created in the patient's eye.

In accordance with the above objects, a novel corneal punch device is provided herein. The corneal punch device comprises a base having an interchangeable corneal cutting block provided thereon supporting a donor's corneal tissue and having an upstanding support member that supports a spring activated moveable piston. The piston carries an interchangeable punch blade such that upon activation, the piston and spring will drive the punch blade through the donor's corneal tissue to provide a corneal button suitable for transplantation onto a patient's eye. The punch blades have various cutting blade surfaces including various diameter round blades and various dimensional non-round or oval blades for cutting either round or other than round corneal buttons from the donor's corneal tissue. The piston, punch blades and corneal cutting block are all keyed together so as to maintain the rotational orientation of the donor's corneal button before, during and after the punching operation. The punch device includes both left and right interchangeable corneal cutting blocks for use with the base.

A novel method of performing a corneal transplant has been invented and is disclosed herein. The method includes the steps of (i) receiving a portion of corneal tissue from a donor wherein the corneal tissue is appropriately marked as coming from the donor's left or right eye and having its twelve o'clock position or particular rotational orientation marked appropriately; (ii) cutting a corneal button from the donor's corneal tissue; and (iii) transplanting such donor's corneal button onto a patient's cornea which has previously had a portion thereof surgically removed wherein such donor's corneal button is positioned in the patient's same left or right eye at the same rotational orientation as it existed in the donor's eye. The method of performing the above corneal transplant operation will reduce the amount of surgically induced astigmatism which normally occurs during a transplant operation.

BRIEF DESCRIPTION OF THE DRAWINGS

The invention will be described in detail with reference to a preferred embodiment thereof, which is a corneal punch system for cutting a corneal button out of a donor's corneal tissue and method of performing a corneal transplant operation. In the drawings:

FIG. 4 is a top view of the corneal block for use in the corneal punch system of the present invention;

FIG. 5 is a side cross-sectional view through section 5—5 of FIG. 4;

FIG. 6 is a cornea scan of a normal eye depicting the various radii of curvature of the eye and showing an outline of the patient's cornea to be removed;

DETAILED DESCRIPTION OF THE INVENTION

Figure 1:
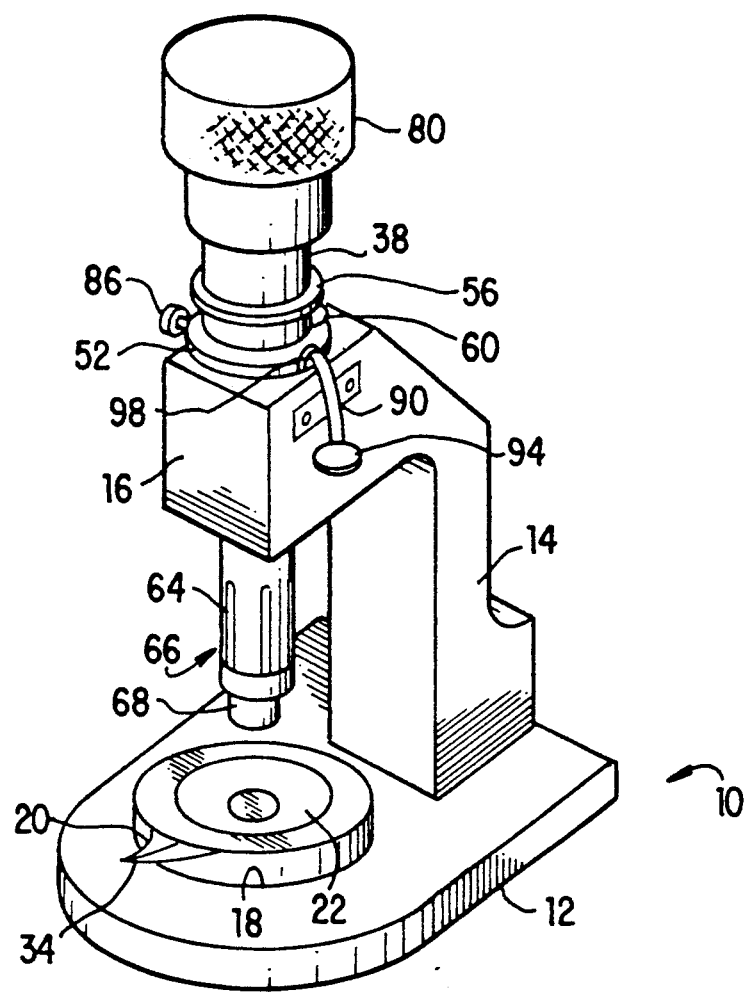
FIG. 1 is a perspective view of the corneal punch system in accordance with the present invention.
Figure 2:
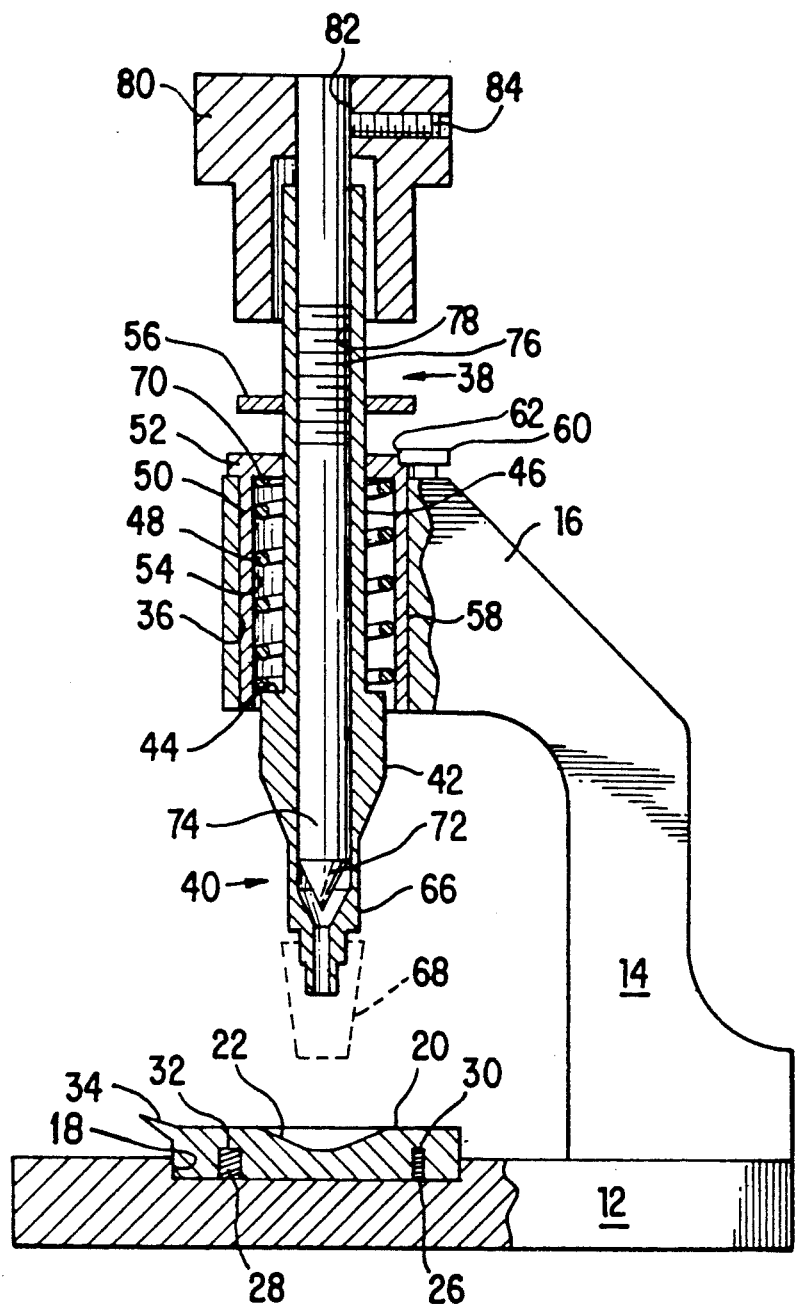
FIG. 2 is a side sectional view of the corneal punch system in accordance with the present invention.
Figure 3:
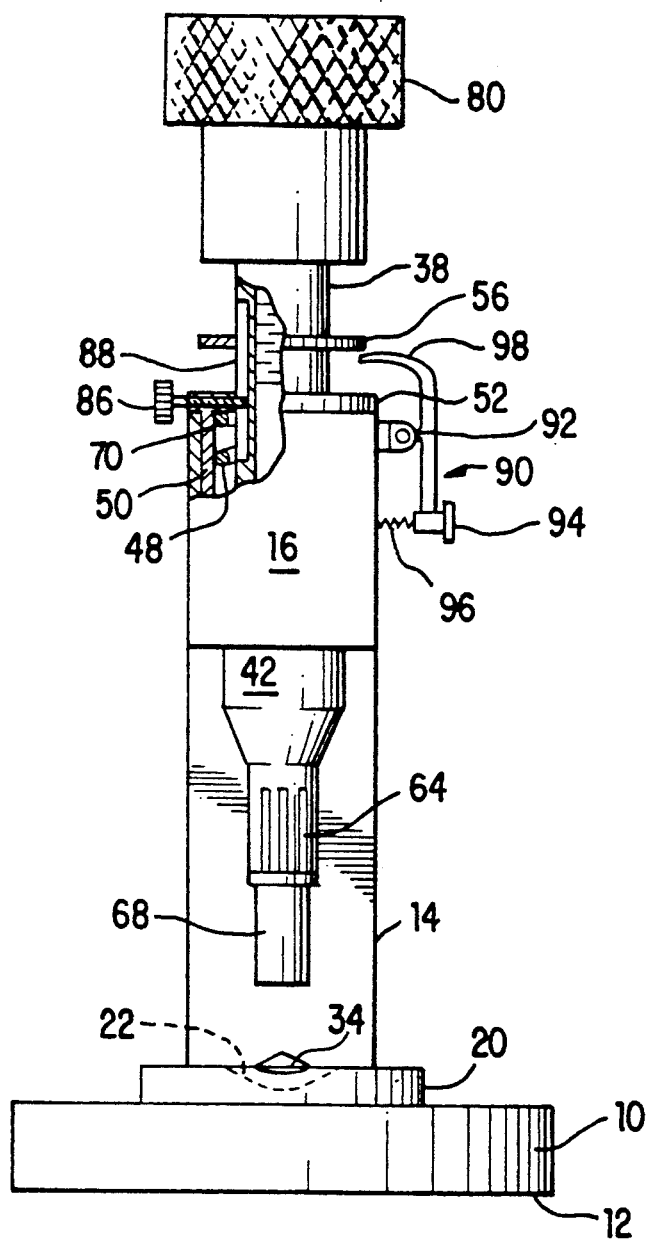
FIG. 3 is a front plan view in partial cross-section of FIG. 2 illustrating the various details of the top of the present invention.

The apparatus of the present invention is a corneal punch system having a base 10 with a flat planar lower surface 12 so that the base 10 will rest firmly on a flat surface as shown in FIGS. 1–3. Affixed to or formed as a part of base 10 is a stand 14 that has a neck 16 extending over a corneal block depression 18 formed in the upper surface of base 10. The depression 18 is formed and adapted to receive and position an interchangeable corneal cutting block 20. The depression 18 has two upstanding pins 26 and 28 having diameters of ⅛ and 3/16 inches, respectively, to properly orient the corneal cutting block 20 into the depression 18.

The cutting block 20 is actually two different cutting blocks, one for the left eye and the other for the right eye. As shown in FIGS. 4 and 5, the cutting block 20 contains a curved concave aspheric depression 22 in the center of its upper surface. Block 20 further has two holes 30 and 32 having diameters of ⅛ and 3/16 inches, respectively, for receiving upstanding pins 26 and 28 of the depression 18 to properly rotationally orientate the corneal cutting block 20 to the base 10. Block 20 further includes an ear 34 to mark the "twelve o'clock" position of cutting block 20 with respect to the donor corneal tissue (not shown) and punching device. Thus, when block 20 is properly positioned in the depression 18 of base 10 as shown in FIG. 2, an aspheric curve is formed therein to receive the donor corneal tissue (not shown) in the proper rotational orientation with respect to the cutting block and corneal punch system. The cutting block 20 is typically manufactured from Nylon, Teflon or Delrin. This construction will assure proper central positioning of the donor tissue in the cutting block as well as maintaining the proper rotational orientation of the donor corneal tissue with respect to the punch device. The cutting blocks for the respective left and right eyes are very similar except for the particular shape of the aspheric curve provided therein which is specifically designed for the specific left or right eye.

The neck 16 on stand 14 is bored to form a cylindrical passageway 36 that accommodates a removable piston indicated generally by the reference numeral 38 that is used to drive a cutting blade 40 through the donor tissue. Passageway 36 also positively positions the piston 38 and the cutting blade 40 so that the cutting blade will move along a defined path to assure an accurate and central cut of the donor tissue positioned on the cutting block 20.

Piston 38 includes a blade holding means 40 at its lowest or most proximal end closest to the corneal cutting block 20, an enlarged diameter portion 42 adjacent the blade holding means 40 defining an upwardly facing shoulder 44, and a reduced diameter distal portion 46. A coil spring 48 is placed about the reduced diameter distal portion 46. A bushing 50 fits slideably over piston 38 and spring 48, the bushing having an enlarged diameter upper integral collar 52 radially extending inside the bushing to form a downwardly facing shoulder 70 supporting the upper end of spring 48 thereagainst. The inner diameter 54 of bushing 50 is slightly larger than the outer diameter of the enlarged diameter piston portion 42 such that the piston will slide axially within bushing 50.

A second collar or piston stop 56 is provided about reduced diameter distal portion 46 and is held in position via a set screw (not shown) such that spring 48 is held under compression.

Bushing 50 has an outer diameter 58 which is slidingly received within passageway 36 of neck 16. In order to hold the bushing 50 and piston 38 in place, there is provided a locking lug 60 in the top surface of the neck 16 immediately adjacent the passageway 36. The upper surface of bushing collar 52 is formed with a cut-out portion 62 (FIG. 2) so that when the piston assembly 38 and bushing 50 are inserted into the passageway 36 with the cut-out portion 62 aligned with the locking lug 60, the bushing and piston assembly can be fully inserted in the passageway 36 until the collar 52 is seated on the neck 16. At that time, the collar 52 is turned slightly so that it will be engaged beneath the locking lug 60 and held in place by it.

The lower end of piston 38 is formed with a blade holding means 40 which includes a plurality of axial slits 64 about its circumference to provide an expanding collet 66. The collet 66 will accommodate a plurality of different cutting blades 68. The cutting blades 68 have a single circular back end which is received on collet 66. The bottom or blade end of cutting blades 68 can have a variety of different circular diameters within the range of 6.0 mm to 10.0 mm or have various non-circular or other than round dimensions for cutting oval or other shaped donor corneal buttons.

Received inside the piston 38 is an expander 72 which has a conically shaped lower end 74 and an externally threaded central portion 76 that is threaded to match threads tapped inside the upper end of piston 38 as shown at 78. As best seen in FIG. 2, the expander 72 is threaded into the piston 38 with the conical-shaped end 74 extending into the collet 66. Thus, as the expander 72 is turned, it will advance downwardly permitting the conically shaped end 74 to expand the collet 66 to, thereby, grip and hold the selected cutting blade 68.

To facilitate the turning of the expander 72, there is provided a knob 80 having a central axial opening 82 which receives the upper end of the expander 72. A set screw 84 will lock the knob 80 and expander 72 together so that when the knob 80 is turned, the expander 72 will also turn. Preferably, the exterior circumferential surface of knob 80 is knurled to facilitate its turning.

However, it is important that the piston 38 and cutting blade 68 not be allowed to rotate in bushing 50. Therefore, bushing collar 52 is provided with a set screw 86 extending radially therethrough, the set screw 86 extending into a longitudinal slot 88 provided in the outer surface of piston 38 as best shown in FIG. 3. The piston 38 is allowed to freely move axially with the set screw 86 extending into slot 88, but is not allowed to rotate relative to the bushing 50 or base 10. It is necessary to prevent rotation of the cutting blade 68 during the punching operation so that the correct rotational orientation of the corneal button can be maintained.

The corneal punch device further includes a cocking lever 90 for cocking the piston 38 in anticipation of cutting the donor corneal tissue. The lever 90 is affixed to the side of the neck 16 with a pivot connection 92 and has proximal and distal ends. The proximal end extends towards the base 10 and has a small knob 94 at its lowermost end facing away from neck 16. A spring 96 is positioned between the neck 16 and knob 94 to bias the knob 94 and proximal lever end away from neck 16. The distal end of lever 90 has a radially inwardly extending hook 98 which, because of spring 96, is biased into contact with piston 38. Hook 98 can be moved axially away from piston 38 by pressing knob 94 and compressing spring 96.

In use, the entire assembly of the knob 80, expander 72, piston 38, spring 48, bushing 50 and piston stop 56 is inserted through the passageway 36 in the neck 16 of stand 14. It will be necessary to push knob 94 laterally towards neck 16 to allow collar 52 and piston stop 56 to pass by hook 98 of cocking lever 90. The cut-out portion 62 of collar 52 is aligned with the locking lug 60 and then the collar 52 is turned slightly so that collar 52 will be engaged beneath the locking lug 60 and held in place by it.

To energize the punch device the knob 80 is then raised while pressing lever knob 94 to allow the piston stop 56 to pass above the lever hook 98. The lever knob 94 is released such that the bottom shoulder of piston stop 56 rests atop the hook 98. To actuate the punch device the cocking lever knob 94 is pressed. thereby releasing piston stop 56 such that spring 48 forces piston 38 and cutting blade 68 downwardly into the cutting block 20 to appropriately cut the donor's corneal tissue without rotation of the cutting blade 68.

The method of performing the novel corneal transplant as disclosed herein is as follows. First, an ophthalmologist must receive from an appropriate eye bank a section of corneal tissue from a donor wherein the tissue is appropriately marked as coming from either the donor's left or right eye and the corneal tissue should be appropriately marked designating the twelve o'clock position or the exact rotational orientation of the tissue as it existed in the donor's eye. This is necessary because as the corneal tissue exists in the eye, the various radii of curvature of the four quadrants (nasal, superior, temporal, inferior) of the cornea differ as can be seen in FIGS. 5, 6-11, as further discussed below. Second, the donor corneal tissue needs to be placed within the corneal cutting block 20 of the corneal punch device such that the twelve o'clock portion or other known reference point is placed appropriately on the ear mark 34 of cutting block 20. The corneal punch device is then operated as disclosed above to cut a corneal button from the donor's corneal tissue such that both during and after the punching procedure the rotational orientation of the corneal button is orientated so that the surgeon will know where the twelve o'clock position or other reference mark is at all times. And, third, the surgeon will transplant the corneal button onto a patient's cornea which has previously had a portion thereof surgically removed wherein such donor's corneal button is positioned in the patient's same left or right eye and in the same rotational orientation as it existed in the donor's eye. In such a manner, it will be possible to perform a corneal transplant operation that will reduce the amount or degree of surgically induced astigmatism which has typically occurred during a transplant operation as performed in accordance with the prior art.

Figure 7:
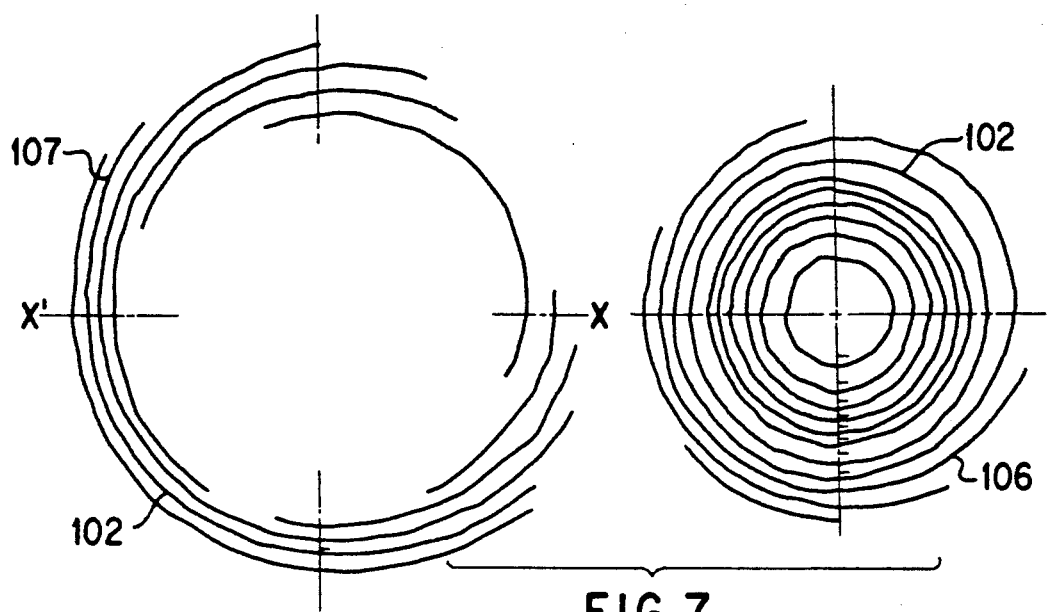
FIG. 7 is the same cornea scan of a normal eye showing a corneal button side by side with the corneal tissue.

The importance of maintaining the correct rotational orientation of the corneal button with respect to the patient's corneal tissue is seen dramatically in FIGS. 6-11. FIGS. 6 and 7 depict a cornea scans of a human cornea 100 which show the various radii of curvature 102 as measured in diopters of the patient's cornea. FIG. 6 is marked with a guide line 104 showing the outline of a corneal button 106 to be cut from the corneal tissue 107. FIG. 7 shows the same cornea as in FIG. 6, except that the corneal button 106 is shown removed from the corneal tissue 107.

Figure 8:
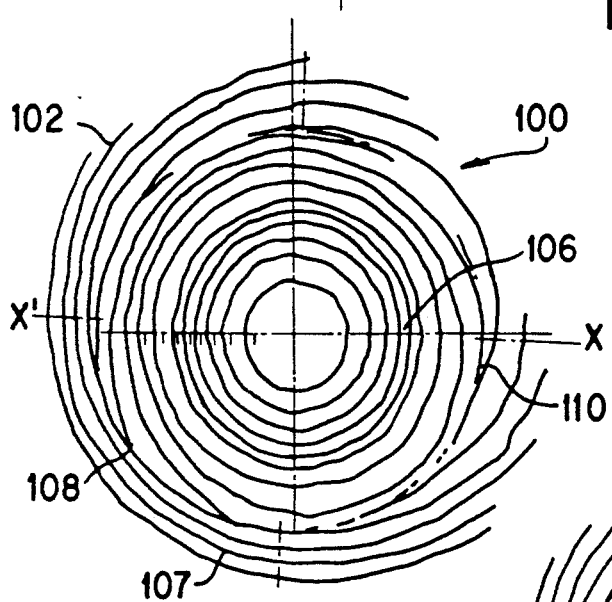
FIG. 8 is a cornea scan of the eye depicting the corneal button positioned with a 90 degree rotational orientation from the original corneal tissue.

FIG. 8 shows the same cornea as in FIG. 6 except that the corneal button 106 has been replaced in the corneal tissue with the corneal button 106 having a 90 degree clockwise rotational orientation to the original tissue. Referring to FIG. 8, it can be seen at 108 and 110 that the radii of curvature of the corneal button 106 do not match those of the original corneal tissue 107, and, therefore, upon surgical reattachment, the cornea will have a surgically induced astigmatism at these points about the periphery of the corneal button 106.

Figure 9:
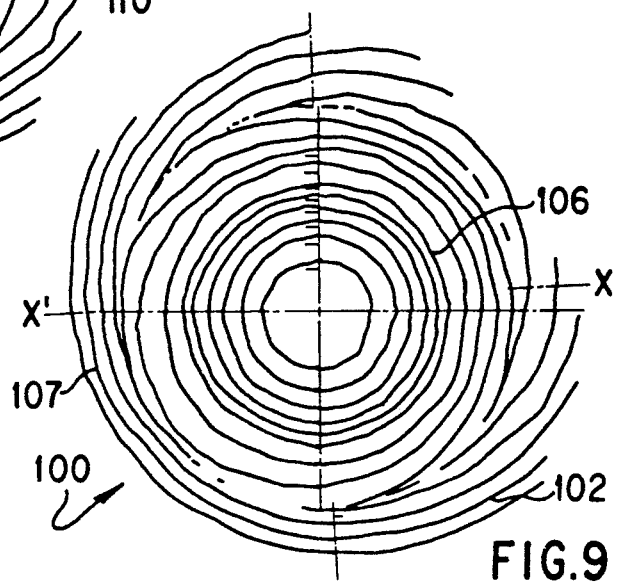
FIG. 9 is a cornea scan of the eye depicting the corneal button positioned with a 180 degree rotational orientation from the original corneal tissue.

Referring to FIG. 9, the corneal button 106 is shown in place with the original corneal tissue 107 wherein the corneal button is at a 180 degree clockwise rotational orientation. Further at 112 and 114, it can be seen that the radii of curvature between the corneal button 106 and corneal tissue 107 are drastically mismatched.

Figure 10:
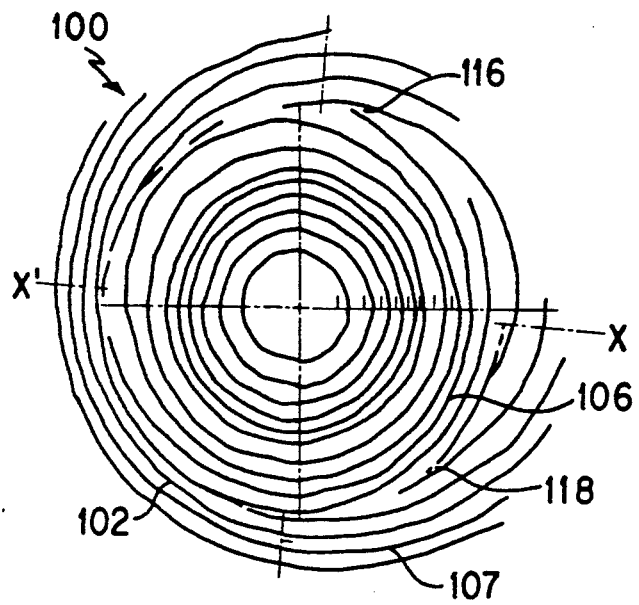
FIG. 10 is a cornea scan of the eye depicting the corneal button positioned with a 270 degree rotational orientation from the original corneal tissue.

Referring to FIG. 10, the corneal button 106 is shown in place with the original corneal tissue 107 wherein the corneal button 106 is at a 270 degree clockwise rotational orientation. Further at 116 and 118, it can be seen that the radii of curvature between the corneal button 106 and corneal tissue 107 are drastically mismatched.

Figure 11:
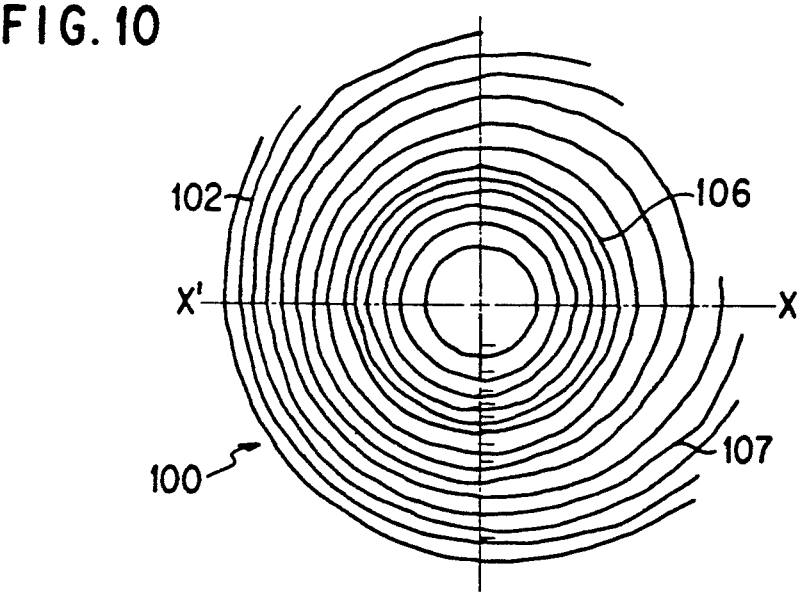
FIG. 11 is a cornea scan of the eye depicting the corneal button positioned with a 360 degree rotational orientation from the original corneal tissue.

However, now referring to FIG. 11, the corneal button 106 is shown in place with the original corneal tissue 107 at a 360 degree clockwise rotational orientation or, in other words, back in the original or correct rotational orientation as shown on FIG. 6. Now, the various radii of curvature 102 match between the corneal button 106 and corneal tissue 102 and, therefore, upon transplantation of such a corneal button into a patient's cornea the amount or degree of surgically induced astigmatism should be greatly reduced or minimized.

Although the present invention has been described with respect to a specific embodiment of the apparatus, it is readily apparent that modifications, alterations, or changes may be made without departing from the spirit and scope of the invention as defined by the following claims.

What is claimed is:

1. A corneal punch for cutting a portion of a cornea of an eye, said corneal punch comprising:
    a support stand having a base portion and an arm portion extending upwardly from said base portion, said base portion defining a recess therein, said base portion having a first pin mounted thereon whereby said first pin extends upwardly from said recess defined in said base portion, said first pin having a first diameter, said base portion having a second pin mounted thereon whereby said second pin extends upwardly from said recess defined in said base portion, said second pin having a second diameter different than said first diameter, said arm portion defining a vertical channel therethrough, said vertical channel being disposed above said recess defined in said base portion;

a piston assembly movably mounted through said vertical channel defined through said arm portion, said piston assembly having a proximal end portion proximal said base portion, said proximal end portion having a means for holding a butting blade disposed thereon;

a means for rotationally locking said piston assembly relative to said arm portion and said base portion, whereby said piston assembly can move axially through said vertical channel defined through said arm portion without rotating relative to said arm portion and said base portion;

a cutting blade mounted on said means for holding a cutting blade; and a cutting block configured to fit within said recess defined in said base portion, said cutting block having an upper surface and a lower surface, said lower surface defining a first recess therein configured to receive and engage said first pin, said lower surface defining a second recess therein configured to receive and engage said second pin, said upper surface of said cutting block defining an aspheric recess therein, said aspheric recess being disposed substantially coaxially to said vertical channel defined through said arm portion when said cutting block is disposed within said recess defined in said base portion and when said first pin and said second pin are disposed within said first recess and said second recess formed on said lower surface of said cutting block, respectively, said aspheric recess being constructed to receive said portion of a cornea of an eye, said upper surface of said cutting block having at least one mark placed thereon, whereby said portion of a cornea of an eye can be placed on said cutting block at a preselected spatial orientation relative to said at least one mark, whereby said portion of a cornea of an eye and said cutting block can be placed on said support stand at a preselected spatial orientation through the use of said first pin and said second pin, and whereby said portion of a cornea of an eye, said cutting block, said support stand, and said piston assembly are maintained in a single rotational orientation throughout operation of said corneal punch.

2. A corneal punch for cutting a portion of a cornea of an eye in accordance with claim 1, wherein said means for holding a cutting blade comprises an expandable collet constructed to retain said cutting blade in a fixed rotational orientation relative to said piston assembly.

3. A corneal punch for cutting a portion of a cornea of an eye in accordance with claim 1, wherein said means for rotationally locking said piston assembly relative to said arm portion comprises a vertically elongated aperture defined through said arm portion adjacent said vertical channel defined through said arm portion, said vertically elongated aperture being dimensioned to receive a pin therethrough, said means for rotationally locking said piston assembly relative to said arm portion further comprising a vertical slot formed on an exterior surface of said piston assembly, said vertical slot being dimensioned to receive said pin therein, whereby said piston assembly is permitted to move axially through said channel defined through said arm portion and whereby said pin prevents rotational movement of said piston assembly relative to said arm portion.

4. A method of performing a corneal transplant comprising the steps of:
placing indicia on a portion of corneal tissue from a donor so as to indicate that said portion of corneal tissue from a donor is from a donor's left eye or right eye and so as to indicate an original rotational orientation of said donor tissue;
cutting a corneal button from said portion of corneal tissue from a donor;
removing a selected portion of corneal tissue from a patient selected to receive said corneal button; and
surgically implanting said corneal button onto said patient's cornea by the steps of:
positioning said corneal button from a donor's left eye or right eye on said patient's left eye or right eye, respectively; and
rotationally orienting said corneal button, whereby said corneal button is oriented in said patient in a transplanted rotational orientation substantially identical to said original rotational orientation of said donor tissue.

5. A method of performing a corneal transplant in accordance with claim 4, wherein said method further comprises the steps of:
mounting said portion of corneal tissue from a donor on a cutting block in a preselected spatial orientation determined by the original rotational orientation of said portion of corneal tissue from a donor;
placing said cutting block on a corneal punch whereby said cutting block and said portion of corneal tissue from a donor are oriented in a preselected spatial orientation relative to said corneal punch; and
cutting said corneal button from said portion of corneal tissue from a donor while simultaneously preventing axial rotation of said portion of corneal tissue from a donor relative to said corneal punch.

* * * * *